United States Patent
Raz et al.

(10) Patent No.: US 11,806,083 B2
(45) Date of Patent: Nov. 7, 2023

(54) CORRECTING MAP SHIFTING OF A POSITION TRACKING SYSTEM INCLUDING REPOSITIONING THE IMAGING SYSTEM AND THE PATIENT IN RESPONSE TO DETECTING MAGNETIC INTERFERENCE

(71) Applicant: BIOSENSE WEBSTER (ISRAEL) LTD., Yokneam (IL)

(72) Inventors: Shaul Haim Raz, Shimshit (IL); Avigdor Rosenberg, Kiryat Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 777 days.

(21) Appl. No.: 15/979,078

(22) Filed: May 14, 2018

(65) Prior Publication Data
US 2019/0343591 A1    Nov. 14, 2019

(51) Int. Cl.
*A61B 34/20*        (2016.01)
*A61B 5/00*         (2006.01)
(Continued)

(52) U.S. Cl.
CPC ............ *A61B 34/20* (2016.02); *A61B 5/6852* (2013.01); *A61B 18/1492* (2013.01);
(Continued)

(58) Field of Classification Search
CPC ... A61B 34/20; A61B 5/6852; A61B 18/1492; A61B 2034/2046; A61B 2090/367;
(Continued)

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

| EP | 2168478 A1 | 3/2010 | |
| EP | 3138485 A1 * | 3/2017 | ............. A61B 5/062 |

(Continued)

OTHER PUBLICATIONS

Van Sint Jan, Serge et al. "In Vivo Registration of Both Electrogoniometry and Medical Imaging: Development and Application on the Ankle Joint Complex", IEEE Transactions On Biomedical Engineering, Apr. 2006, pp. 759-762, vol. 53, No. 4.

(Continued)

*Primary Examiner* — Christopher Koharski
*Assistant Examiner* — Richmond J Van Winter
(74) *Attorney, Agent, or Firm* — Dergosits & Noah LLP; Todd A. Noah

(57) ABSTRACT

A system includes a processor and an output device. The processor is configured to: (a) receive electrical signals indicative of measured positions of (i) one or more chest position sensors attached externally to a chest of a patient, and (ii) one or more back position sensors attached externally to a back of the patient; (b) compare between (i) a first shift between the measured positions and respective predefined positions of the one or more chest position sensors, and (ii) a second shift between the measured positions and respective predefined positions of the one or more back position sensors; and (c) produce an alert in response to detecting a discrepancy between the first and second shifts. The output device is configured to output the alert to a user.

20 Claims, 3 Drawing Sheets

(51) Int. Cl.
*A61B 18/14* (2006.01)
*A61B 5/0215* (2006.01)
*A61B 18/00* (2006.01)
*A61B 90/00* (2016.01)

(52) U.S. Cl.
CPC ... *A61B 5/0215* (2013.01); *A61B 2018/00392* (2013.01); *A61B 2018/00869* (2013.01); *A61B 2034/2046* (2016.02); *A61B 2090/367* (2016.02); *A61B 2090/378* (2016.02)

(58) Field of Classification Search
CPC ............ A61B 2090/378; A61B 5/0215; A61B 2018/00392; A61B 2018/00869; A61B 2090/376; A61B 2034/2053; A61B 2018/00666; A61B 2018/00636; A61B 2034/2051; A61B 2017/00053; A61B 5/1126; A61B 5/113; A61B 5/1121; A61B 5/11; A61B 5/70; A61B 2017/00119; A61B 2018/00898; A61B 2018/00577; A61B 18/12; A61B 5/0422; A61B 2018/00351; A61B 2018/00595; A61B 2034/2072; A61B 2034/2059; A61B 2018/0066; A61B 5/287
See application file for complete search history.

(56) References Cited

U.S. PATENT DOCUMENTS

| | | | |
|---|---|---|---|
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2009/0281417 | A1* | 11/2009 | Hartmann ............... A61B 34/20 600/424 |
| 2009/0295800 | A1 | 12/2009 | Vetter et al. |
| 2010/0079158 | A1* | 4/2010 | Bar-Tal .................. A61B 5/062 324/705 |
| 2012/0296202 | A1 | 11/2012 | Mountney et al. |
| 2015/0018668 | A1 | 1/2015 | Mershon et al. |
| 2015/0272688 | A1* | 10/2015 | Blair .................. G06K 7/10386 340/10.2 |
| 2016/0367323 | A1* | 12/2016 | Malinin ................. A61B 34/20 |
| 2017/0065205 | A1* | 3/2017 | Ludwin ................ A61B 5/6833 |
| 2017/0325895 | A1* | 11/2017 | Krimsky ............... A61B 34/20 |
| 2018/0325603 | A1* | 11/2018 | Govari .................... A61B 5/062 |
| 2019/0343421 | A1* | 11/2019 | Yanof .................... A61B 5/746 |

FOREIGN PATENT DOCUMENTS

| | | |
|---|---|---|
| EP | 3138485 A1 | 3/2017 |
| WO | WO 96/05768 A1 | 2/1996 |
| WO | WO 2009137558 A2 | 11/2009 |

OTHER PUBLICATIONS

Extended European Search Report for corresponding EPA No. 19174130.5 dated Sep. 18, 2019, pp. 7 (Copy Provided).

* cited by examiner

CORRECTING MAP SHIFTING OF A POSITION TRACKING SYSTEM INCLUDING REPOSITIONING THE IMAGING SYSTEM AND THE PATIENT IN RESPONSE TO DETECTING MAGNETIC INTERFERENCE

FIELD OF THE INVENTION

The present invention relates generally to medical devices, and particularly to methods and systems for detecting and correcting map shifting in position tracking systems.

BACKGROUND OF THE INVENTION

Various techniques for visualizing and mapping coordinates of medical systems are known in the art.

For example, U.S. Patent Application Publication 2012/0296202 describes a method and system for registering ultrasound images and physiological models to x-ray fluoroscopy images. A fluoroscopic image and an ultrasound image, such as a Transesophageal Echocardiography (TEE) image, are received. A 2D location of an ultrasound probe is detected in the fluoroscopic image. A 3D pose of the ultrasound probe is estimated based on the detected 2D location of the ultrasound probe in the fluoroscopic image.

U.S. Patent Application Publication 2015/0018668 describes a method that includes registering a fluoroscopic imaging system and a position tracking system to a common frame of reference. A region of interest is marked in a patient body by the position tracking system. Using the common frame of reference, a field of view of the fluoroscopic imaging system is set such that the region of interest appears in the field of view.

SUMMARY OF THE INVENTION

An embodiment of the present invention that is described herein provides a system that includes a processor and an output device. The processor is configured to: (a) receive electrical signals indicative of measured positions of (i) one or more chest position sensors attached externally to a chest of a patient, and (ii) one or more back position sensors attached externally to a back of the patient; (b) compare between (i) a first shift between the measured positions and respective predefined positions of the one or more chest position sensors, and (ii) a second shift between the measured positions and respective predefined positions of the one or more back position sensors; and (c) produce an alert in response to detecting a discrepancy between the first and second shifts. The output device is configured to output the alert to a user.

In some embodiments, the processor is configured to receive each of the measured positions after receiving the predefined positions. In other embodiments, the processor is configured to estimate distances between the measured positions and the respective predefined positions, and to detect the discrepancy based on the estimated distances. In yet other embodiments, the processor is configured to detect the discrepancy by detecting that at least one of the distances between a predefined position and a respective measured position is above a predefined threshold value.

In an embodiment, the output device is configured to display at least one value of the distances. In another embodiment, the processor is configured to initiate, based on the alert, a responsive action for reducing the discrepancy. In yet another embodiment, the processor is configured to: (i) calculate, based on the predefined positions, a predefined geometrical center-of-gravity (COG), (ii) calculate, based on the measured positions, a measured geometrical COG, (iii) compare between the measured geometrical COG and respective predefined geometrical COG of the given set, and (iv) produce the alert in response to detecting a discrepancy between the measured geometrical COG and the predefined geometrical COG.

There is additionally provided, in accordance with an embodiment of the present invention, a method including, receiving electrical signals indicative of measured positions of (i) one or more chest position sensors attached externally to a chest of a patient, and (ii) one or more back position sensors attached externally to a back of the patient. A comparison is carried out between (i) first shift between the measured positions and respective predefined positions of the one or more chest position sensors, and (ii) a second shift between the measured positions and respective predefined positions of the one or more back position sensors. An alert is produced in response to detecting a discrepancy between the first and second shifts. The alert is output to a user. The present invention will be more fully understood from the following detailed description of the embodiments thereof, taken together with the drawings in which:

DETAILED DESCRIPTION OF EMBODIMENTS

Overview

Figure 1:
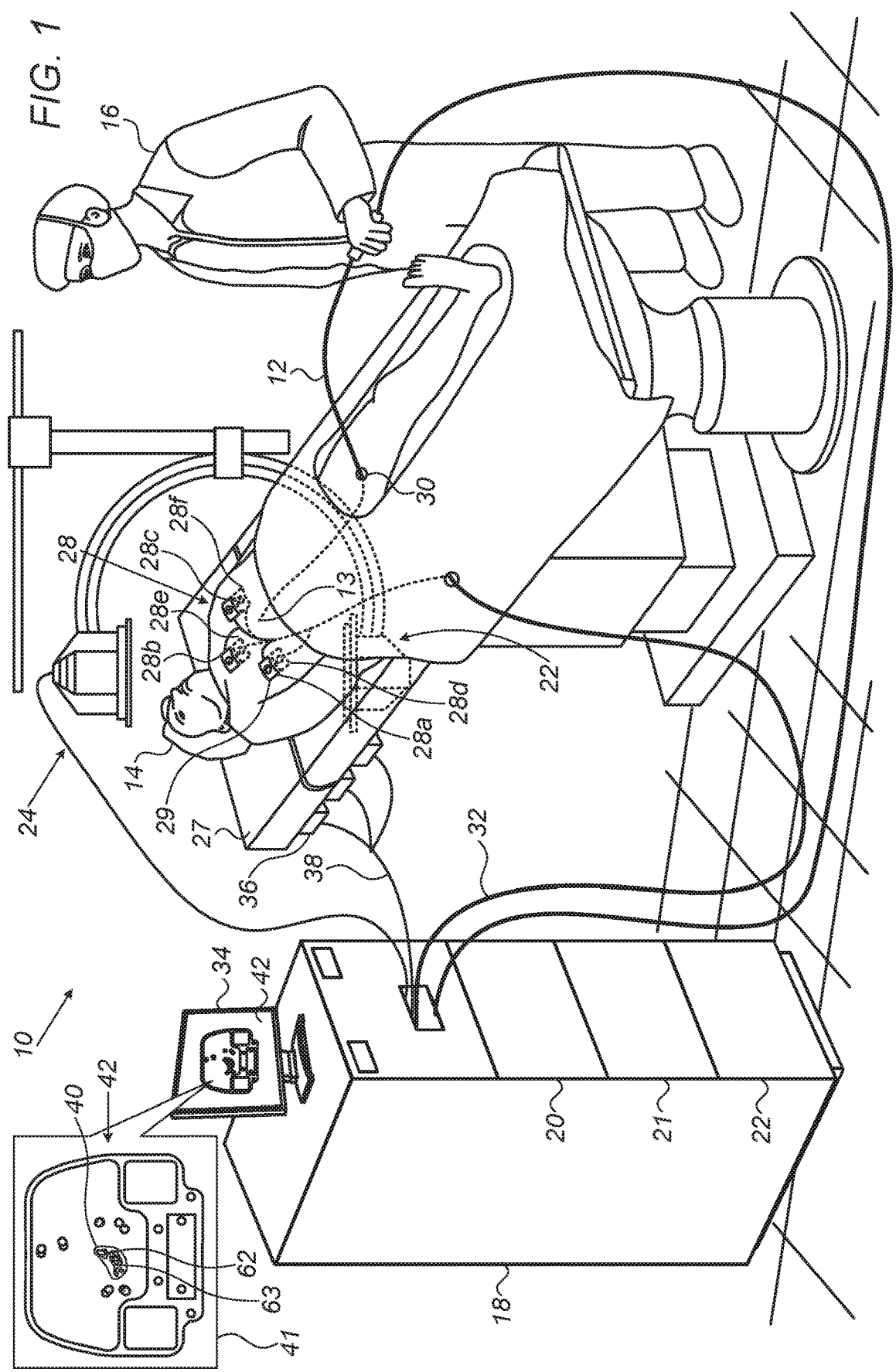
FIG. 1 is a schematic, pictorial illustration of a system for catheterization of a patient heart, in accordance with an embodiment of the present invention.

Embodiments of the present invention that are described hereinbelow provide improved methods and systems for detecting and correcting a map shifting that occurs during a medical procedure, such as a cardiac ablation.

An ablation procedure typically involves navigating an ablation catheter to one or more positions in a patient heart for creating an electropotential (EP) map of the heart, to be used later in carrying out the actual ablation. The navigation of the catheter may be carried out using any suitable position tracking system, such as a magnetic position tracking system.

In some cases, a position map shifting may be caused, for example, by a movement of patient, or by metallic objects interfering with the magnetic position tracking system. As a result, the catheter may be displayed at a wrong position over the image of the heart. Failure to detect and correct such map shifts may result in a discrepancy between the measured position and the actual position of the ablation catheter, which may require repeating the mapping procedure and thus extending the cycle time of the ablation procedure.

Note that even if a user of the ablation system, e.g., a physician, is aware of a map shifting event, he typically has no means for correcting the shift accurately. For example, the shift may occur when the patient lifts his/her shoulder during the ablation, e.g., due to pain associated with the ablation, or for any other reason. In this example, the physician may attempt to reposition the moving shoulder, but possibly not accurately to the original position.

In some embodiments, a system for detecting and correcting map shifting comprises multiple patches attached externally to the patient torso, which are typically used for the navigation purposes. In some embodiments, six patches may be used, three back patches attached to the patient back, forming a geometrical triangle, and three chest patches are attached to the patient chest, each may be facing the respective back patch.

In some embodiments, each of the patches comprises a magnetic position sensor configured to produce position signals indicative of the position of the respective patch in the coordinate system of the magnetic position tracking system.

In some embodiments, the map shifting correcting system comprises a processor configured to receive the position signals during the mapping and ablation procedure. Initial positions of the patches that are measured before performing the mapping are referred to herein as "predefined positions", and the positions of the patches measured further-on during the ablation procedure are referred to herein as "measured positions". In case of six patches, there are six predefined positions and six respective measured positions.

In some embodiments, the processor is configured to compare between the relative positions of the chest patches sensors and the relative positions of the back patches sensors of the measured positions and the respective predefined positions. The processor is further configured to produce a near real-time (RT) alert in response to detecting a discrepancy between the measured and predefined relative positions of at least one of the chest position sensors relative to the back position sensors.

In some embodiments, the processor is further configured to display to the user both the predefined and the measured positions, so that the user may correct the map shifting by moving the patient torso to an appropriate posture.

The disclosed techniques provide the user with a near RT alert of a map shifting event and a responsive action carried out by the processor or by the user, for correcting the map shifting accordingly, thereby improving the position tracking accuracy and reducing the overall cycle time of ablation procedures.

System Description

FIG. 1 is a schematic, pictorial illustration of a system 10 for electro-physiological mapping and ablating of a patient heart 40, in accordance with an embodiment of the present invention.

In some embodiments, system 10 comprises a medical probe, such as a catheter 12, comprising a distal tip 13 that comprises a plurality of devices (not shown), such as a magnetic position sensor and/or an impedance sensor. During the mapping phase, a physician 16 inserts catheter 12, via an insertion point 30, into the vasculature of a patient 14, and navigate the catheter tip to the patient's heart based on the position sensor of the magnetic position tracking system. Subsequently, catheter 12 is used for EP mapping and later ablating tissue of heart 40.

In some embodiments, console 18 comprises a memory 22 and a processor 20, which is typically a general-purpose computer, with suitable front end and interface circuits for receiving signals from catheter 12 and for controlling the other components of system 10 described herein.

Processor 20 may be programmed in software to carry out the functions that are used by the system, and the processor stores data for the software in memory 22. The software may be downloaded to console 18 in electronic form, over a network, for example, or it may be provided on non-transitory tangible media, such as optical, magnetic or electronic memory media. Alternatively, some or all of the functions of processor 20 may be carried out by dedicated or programmable digital hardware components.

In some embodiments, system 10 further comprises a magnetic position tracking system, and/or an impedance-based active current location (ACL) system. Each of these systems may be used for tracking the position of distal tip 13 for the purpose of navigating catheter 12 to EP mapping and ablation locations within heart 40 of patient 14.

In some embodiments, the magnetic position tracking system comprises a location pad (not shown) comprising multiple (e.g., three) magnetic field-generators 36 placed at known positions external to patient 14, e.g., below the patient's back lying on a table 27, or below table 27. In an embodiment, console 18 assists in carrying out the techniques described herein.

In some embodiments, console 18 comprises a driver circuit 21, configured to drive field-generators 36 via a cable 38. When distal tip 13 is navigated by physician 16 into heart 40, the magnetic position sensor at distal tip 13, generates position signals in response to the sensed external magnetic fields produced by field-generators 36, thereby enabling processor 20 to identify the position of distal tip 13 within the cavity of heart 40.

The magnetic position sensor at the distal tip is connected to interface circuitry integrated with processor 20 at the catheter proximal end. In an embodiment, the position of distal tip 13 is shown on an image 42 of heart 40, which is displayed on a user display 34. In some embodiments, image 42 is acquired using an anatomical imaging system, such as a fluoroscopic imaging system 24 or any other suitable imaging technique. Fluoroscopic imaging system 24 is connected to the magnetic position tracking system via console 18.

In an embodiment, fluoroscopic imaging system 24 is typically positioned in a base position relative to patient 14, at a certain height above the patient chest. For example, in an anterior-posterior (AP) position orthogonal to patient chest, or in any other suitable angle relative to the patient chest. During the procedure, an operator (e.g., physician 16) may move system 24 to an image acquisition position shown in FIG. 1, which is typically closer to patient 14, so as to acquire image 42.

This method of magnetic-field based position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, system 20 comprises a plurality of position sensors 28, which are coupled to the body of patient 14, e.g., using patches 29 that adhere to the skin of patient 14. In other embodiments, an additional electrode, such as impedance measurement electrode (not shown) or any other suitable electrode may be coupled to at least one patch 29.

In the example of FIG. 1, system 10 comprises six position sensors, of which position sensors 28a, 28b, and 28c are coupled to the front (e.g., chest) of patient 14, and position sensors 28d, 28e, and 28f are coupled to the back of patient 14.

In other embodiments, system 10 may comprise any suitable number of position sensors, coupled to the patient skin in any suitable arrangement.

In an embodiment, each position sensor 28 produces a signal indicative of the position of a respective patch 29 in the coordinate system of the magnetic position tracking system.

Position sensors 28 of respective patches 29 are typically connected, via a cable 32, to processor 20, which is configured to receive position signals from the position sensors. Based on the position signals, processor 20 is configured to estimate the position of each patch 29.

Display 34, is typically configured to facilitate performance of the mapping and/or ablation procedures by displaying relevant information to physician 16. For example, based on the position signals processor 20 is configured to display the locations of patches 29 and distal tip 13 of catheter 13 within image 42, e.g., by superimposing icons representing distal tip 13 and catheter 12 over image 42, as will be depicted in detail in FIG. 2 below.

Reference is now made to an inset 41, which is a magnification of image 42. As described above, the estimated locations of catheter 12 and distal tip 13 may be indicated to the physician as suitable icons, such as marker 62 (indicative of catheter 12) and marker 63 (indicative of distal tip 13) on display 34. Based on this indication, physician 16 may navigate distal tip 13 of catheter 12 to one or more desired locations within heart 40.

In other embodiments, only marker 63 may be displayed on display 34, whereas catheter 12 may have position sensors coupled only to distal tip 13. In alternative embodiments, fluoroscopic imaging system 24 may be used to acquire an image of catheter 12 in heart 40, so that processor 20 may display marker 62 based on the acquired image.

In some embodiments, the medical (EP mapping and/or ablation) procedure starts by measuring the initial positions of position sensors 28a-28f mounted on patches 29. In some embodiments, processor 20 is configured to store these initial positions, referred to herein as "predefined positions," for example, in memory 22 or in an internal memory of processor 20.

During the EP mapping and/or ablation procedure, physician 16 navigates distal tip 13 to visit multiple locations within heart 40, so as to carry out the EP mapping or the ablation procedures. In some embodiments, processor 20 is configured to receive from catheter 12, at each of the visited locations, position coordinates of the visited locations as measured by the magnetic position tracking system. At the same time, processor 20 also receives from position sensors 28, position signals indicative of the positions of respective patches 29.

In some embodiments, processor 20 is configured to display, on display 34 or any other suitable output device, the currently measured positions of each patch 29 and distal tip 13, overlaid on image 42.

Typically, processor 20 comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Providing Alert of Map Shifting and Responsive Action

Figure 2:
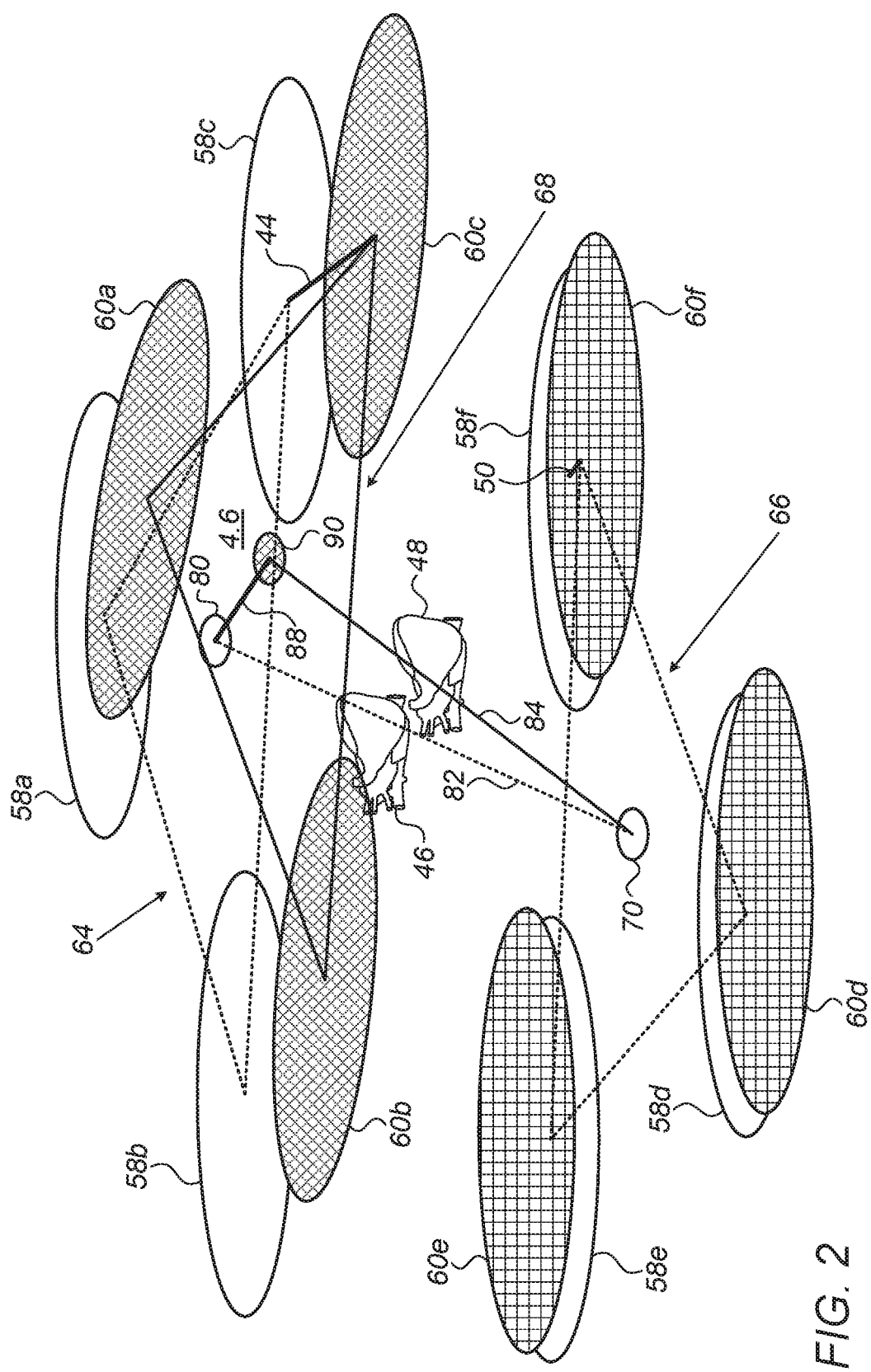
FIG. 2 is a schematic, pictorial illustration of patch icons overlaid on a patient heart image, in accordance with an embodiment of the present invention.

FIG. 2 is a schematic, pictorial illustration of icons 58 and 60, which are indicative of the positions of respective patches 29, overlaid on image 42, in accordance with an embodiment of the present invention.

In some embodiments, processor 20 is configured to visualize the predefined and measured positions of position sensors 28a-28f. For example, processor 20 is configured to display icons 58 and 60 on display 34 so as to indicate the predefined and measured positions of position sensors 28, respectively, as will be described in detail below.

In some embodiments, icons 58a-58f are indicative of the predefined position of patches 29 having respective position sensors 28a-28f coupled thereto. Icons 58a-58c are indicative of the predefined position of respective position sensors 28a-28c, referred to herein as chest position sensors, coupled to the chest of patient 14. Icons 58d-58f are indicative of the predefined position of respective position sensors 28d-28f, referred to herein as back position sensors, coupled to the back of patient 14.

Processor 20 is configured to store the predefined position values of position sensors 28a-28f acquired in a memory, for example, in an initialization step of the medical procedure, and to display respective icons 58a-58f overlaid, for example, on image 42.

Note that chest position sensors 28a-28c are moving due to respiration cycles of patient 14. In some embodiments, processor 20 is configured to collect multiple position measurements of chest position sensors 28a-28c over a period of time, and to apply various statistical tools, such as averaging, so as to estimate the positions of icons 58a-58c.

In some embodiments, processor 20 is configured to produce a body coordinate system (BCS) whose origin is based on the positions of patches 29. In the example of FIG. 2, the centers of icons 58d-58f that visualize respective back position sensors 28d-28f, are positioned on the vertices of a virtual triangle 66. In some embodiments, the origin of the BCS may be determined, for example, based on a point 70, which is a geometrical center-of-gravity (COG) of virtual triangle 66. The term "geometrical COG" is referred to below simply as "COG" for brevity.

In other embodiments, the origin of the BCS may be determined based on the position signals received from a selected position sensor among back position sensors 28d-28f. Note that the positions on icons 58 in the BCS are determined based on: (a) the position signals received from position sensors 28 and, (b) an estimated vector between a COG (not shown) of field-generators 36 and point 70 of the BCS.

During the medical procedure, the back of patient 14 is typically substantially static relative to the COG of field-generators 36, therefore, point 70 is substantially stationary in the coordinate system of the magnetic position system. In exemplary cases, the position of chest position sensors 28a-28c and heart 40, may shift relative to point 70, for example when patient 14 lifts a shoulder.

In these cases, the shifted position of heart 40 may cause map shifting between the predefined and measured positions described above. Failure to detect and correct such map shifts may result in faulty position tracking of distal tip 13 and, in severe cases, may require repeating the mapping procedure and extending the cycle time of the medical procedure.

In the example of FIG. 2, heart 40 is shifted from an initial position shown as a schematic icon 46, to a shifted position shown as a schematic icon 48. Note that schematic icons 46 and 48 are shown in FIG. 2 for the sake of clarity and may not be actually displayed in image 42. In other embodiments, images of heart 40 may be acquired before and after the shift, for example using fluoroscopy imaging system 24, and displayed by processor 20 on display 34.

In some embodiments, processor 20 is configured to display icons 60a-60f, indicative of the presently measured position of respective position sensors 28a-28f mounted thereon. Icons 60a-60c are indicative of the currently measured positions of respective chest position sensors 28a-28c, and icons 60d-60f are indicative of the currently measured positions of respective back position sensors 28d-28f. In the context of the present disclosure and in the claims, the terms "currently measured" and "measured" are used interchangeably and refer to the current position of one or more given patches 29 measured using respective position sensors 28.

In the example of FIG. 2, icons 58a-58c, representing the predefined respective position of chest position sensors 28a-28c, are arranged in a virtual triangle 64, such that the centers of icons 58a-58c are positioned on the vertices of triangle 64. In some embodiments, processor is configured to calculate (and optionally display) point 80, indicative of the geometrical COG of triangle 64, and to calculate a vector 82 between points 70 and 80.

Similarly, the centers of icons 60a-60c, representing the current respective positions of chest position sensors 28a-28c, are positioned on the vertices of a virtual triangle 68. In some embodiments, processor 20 is configured to calculate (and optionally display) point 90, indicative of the COG of triangle 68, and to calculate a vector 84, between points 70 and 90.

In some embodiments, processor 20 is configured to estimate a distance 88 between points 80 and 90, which is indicative of the level of map shifting caused by the move of the patient shoulder. In an embodiment, processor 20 may calculate distance 88 by subtracting between vectors 82 and 84.

In some embodiments, processor 20 is configured to store, e.g., in memory 22, a specified threshold value, to be compared with the distance, so as to determine whether the distance between points 80 and 90 is within the specified threshold value. For example, the specified threshold value may be determined to 4 mm.

In the example of FIG. 2, processor 20 is configured to compare between distance 88, which is 4.6 mm, and the threshold value. In response to detecting that distance 88 exceeds the threshold value, processor 20 is configured to produce an alert to the operator of system 10 (e.g., physician 16).

In some embodiments, the alert is displayed as the value of distance 88, as shown in FIG. 2. In other embodiments, the alert may be indicated using any other suitable form, such as by overlaying on image 42 a text comprising an error code, displaying distances that do not exceed the threshold value in green color and the distance that exceeds the threshold value in red color.

As described above, the relative positions between position sensors 28a-28f may change due to unintended move of the torso of patient 14, which moves patches 29 relative to one another. In other cases, metallic objects (e.g., fluoroscopic imaging system 24 or another medical tool or system) may cause interference in the magnetic fields of the magnetic position tracking system. In some embodiments, processor 20 is configured to detect the map shifting and may assist the operator of system 10 to identify the source causing the map shifting, and to correct the shift.

In some embodiments, instead of comparing between COGs, such as points 70, 80 and 90, processor 20 is configured to compare between the positions of any selected positions of the predefined positions and respective measured positions of position sensors 28a-28f, and to output the positions and the comparison result, for example, to display 34. In an example embodiment, processor 20 is configured to calculate a distance 44, which is the distance between the centers of icons 58c and 60c, and is indicative of the position shift of chest position sensor 28c. In this example, processor 20 is configured to compare between the shift of point 70 and distance 44.

In another example, Processor 20 is configured to calculate a distance 50, indicative of the position shift of back position sensor 28f located in front of chest position sensor 28c, and to compare between distances 44 and 50. The same comparison may be carried out between any position sensors, such as between position sensors 28a and 28d, and between position sensors 28b and 28e.

In some embodiments, processor 20 is configured to store a specified threshold value, to be compared with the distance, so as to determine whether the distance between each pair of icons 58 and 60 is within the specified threshold value, e.g., 4 mm. In case the torso of patient 14 moves as a rigid body, such that all measured distances are above 4 mm but substantially similar in distance and direction, processor 20 will not issue an alert.

In some embodiments, processor 20 is configured to store a threshold value for each of the comparisons described above. The thresholds value may be different for each comparison.

In some embodiments, processor 20 is configured to output a display according to value of distance relative to the threshold. In some embodiments, processor 20 supports threes display modes as follows: (i) displaying only the value of the distance in case the value is below the specified threshold value. This display mode indicates that registration is within the specification. (ii) Displaying an underline below the value of the distance, which indicates that the value of the distance is above the specified value, however the respective patch is adhered to the chest and therefore is not suspected as causing a registration problem. (iii) Displaying a frame surrounding the value of the distance, which indicates that the value of the distance is above the specified value for a patch adhered to the back of patient 14.

This display mode indicates that processor 20 detected a discrepancy between the measured and predefined positions, which may indicate patient change of posture that may cause a map shift. In other words, the shift between the at least one of the chest position sensors and the BCS exceeds the specification and a responsive action is required. In some of these embodiments, processor 20 is further configured to display an arrow (not shown) indicating the direction of the map shifting. In other embodiments, processor 20 may support any other suitable display modes, which may be predefined or configured by the user of system 10.

As described above, metallic objects may cause interference in the magnetic fields of the magnetic position tracking system, resulting in a discrepancy between the measured and predefined positions of one or more position sensors 28. The inventors found that such interferences may cause shifts between predefined and measured positions of respective patches 29 to distance values substantially larger than 4 mm.

In some embodiments, processor 20 is configured to determine whether the source of the discrepancy is a field interference or another source, such as movement of a shoulder or another part of the patient torso. In order not to falsely alert on a map shift, processor 20 is required to identify the source of the movement of sensors 28.

In some embodiments, processor 20 is configured to detect magnetic interference using various methods, such as but not limited to, location convergence figure of merit of a location algorithm.

In response to detecting a magnetic interference in one or more of position sensors 28d-28f, processor 20 is configured to output an alert of the detected discrepancy. Processor 20 may further display a message (e.g., on display 34) suggesting the operator of system 10 (e.g., physician 16) to move fluoroscopic system 24 to a distance larger than the currently used distance from the chest position sensors, or, for example, to the base position described above.

In example embodiments, in response to detecting a distance values larger than a threshold, e.g. 4 mm between points 80 and 90, processor 20 is configured to display an arrow (not shown), indicative of the direction caused by the map shifting, for example, by moving a left shoulder of patient 14. In these embodiments, physician 16 or any other authorized person, may move the left shoulder of patient 14 in a direction opposite to the direction of the arrow so as to correct the shift and resume the mapping or procedure.

The icons, markers and alerts displayed in FIG. 2 are shown by way of example, in order to illustrate certain problems that are addressed by embodiments of the present invention and to demonstrate the application of these embodiments in enhancing the performance of system 10.

Embodiments of the present invention, however, are by no means limited to these specific sort of examples. In other embodiments, distance values showing a discrepancy between the measured and predefined positions, may have a different color. For example, white and red colors for distance values below and above 4 mm, respectively.

Furthermore, processor 20 is configured to output an alert of the detected discrepancy in any suitable manner, such as, but not limited to text, sound, image or a three-dimensional (3D) representation.

Figure 3:
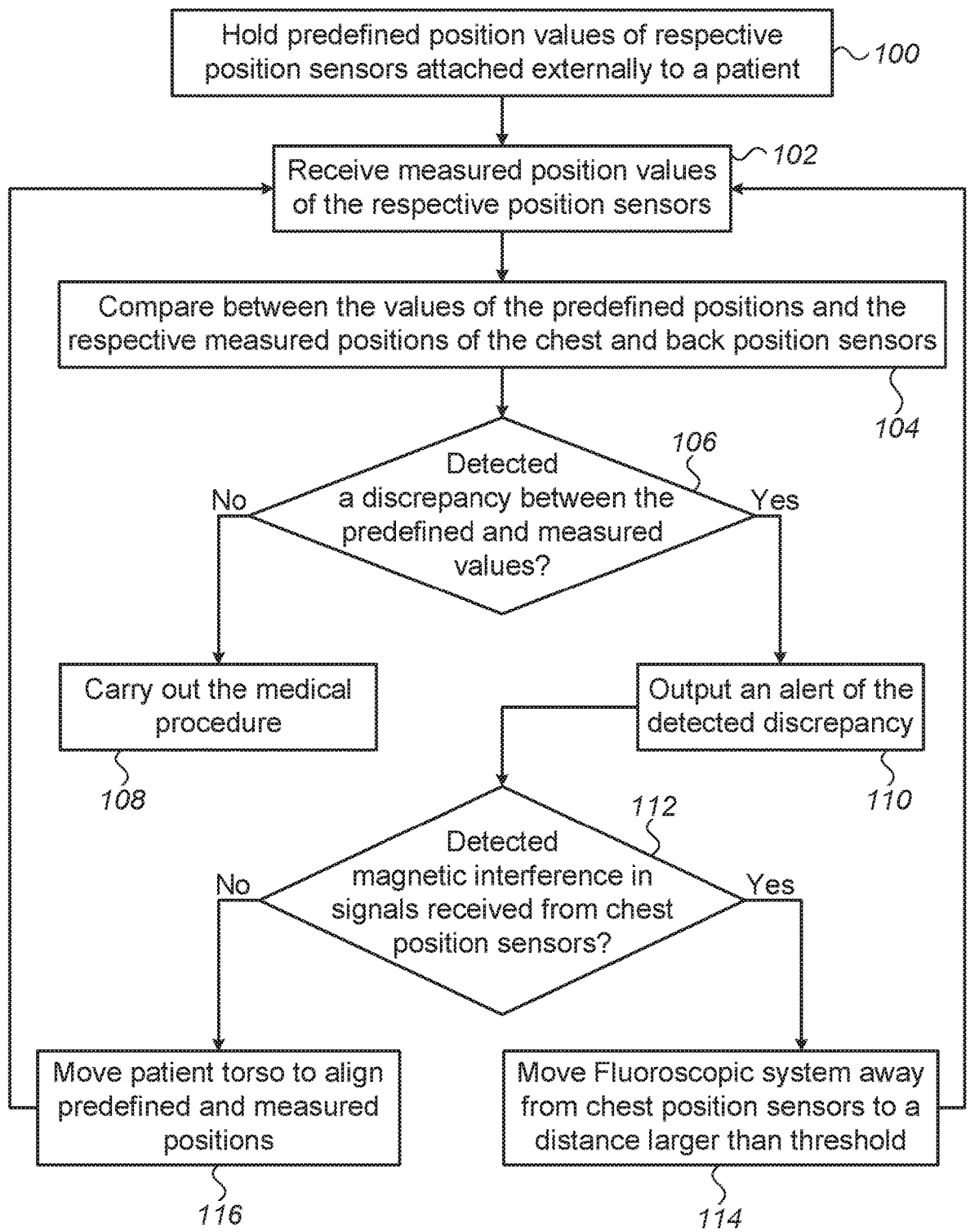
FIG. 3 is a flow chart that schematically illustrates a method for alerting and correcting map shifting, in accordance with an embodiment of the present invention.

FIG. 3 is a flow chart that schematically illustrates a method for alerting and correcting a discrepancy between the measured and predefined relative positions of one or more patches adhered to the body of patient 14, in accordance with an embodiment of the present invention.

The method begins at a predefined position holding step 100, with processor 20 receiving and holding initial (denoted "predefined") position values of position sensors 28a-28f attached externally to patient by respective patches 29. In some embodiments, the predefined position values of position sensors 28a-28f are acquired as part of an initialization of the medical procedure, or the position tracking carried out during the procedure. At a measured position acquisition step 102, during the medical procedure, processor 20 receives position signals indicative of the current respective positions of sensors 28a-28f.

At a comparison step 104, processor 20 compares between the predefined positions and the measured positions of the respective position sensors. In the example of FIG. 2, point 80 is indicative of the COG of triangle 64, and point 90 is indicative of the COG of triangle 68. In this example, a distance of 4.6 mm is measured by processor 20, as distance 88 between points 80 and 90.

At a detection step 106, processor 20 checks whether there is a discrepancy between the predefined and measured positions. In some embodiments, processor 20 compares between the threshold value, e.g., 4 mm, and distance 88 estimated at comparison step 104 above, which is proportional to the map shifting occurred during the medical procedure. In these embodiments, processor 20 detects a discrepancy between the predefined and measured positions when the estimated distance is larger than the threshold value. If no discrepancy detected, the method continues to a procedure performing step 108, in which the operator (e.g., physician 16) applies system 10 to carry out the medical procedure.

In the example of FIG. 2, a discrepancy was detected between points 80 and 90 indicating a map shifting, measured by the value of distance 4.6 mm, which is above the threshold value of 4 mm. At an alert outputting step 110, processor 20 outputs an alert of the detected discrepancy.

In some embodiments, processor 20 is further configured to display, on display 34, an error code number (not shown) indicative of the type of discrepancy detected by processor 20. For example, a discrepancy detected on a single position sensor (e.g., position sensor 28d) receives a given error code number, and a discrepancy detected between COGs of two respective triangles laid out between multiple position sensors 28, e.g., between points 80 and 90, receives a different error code number.

As described in FIG. 2 above, the discrepancy may be caused by an interference in the magnetic fields of the magnetic position tracking system. In the configuration of system 10, when fluoroscopic imaging system 24, which typically comprises metallic parts, is at an operative position, some of the metallic parts are in close proximity to patches 29 and to field-generators 36, and therefore, may cause magnetic interference.

At an interference checking step 112, processor 20 checks whether magnetic interference is detected in signals received from chest position sensors 28a-28c. If interference is detected, processor 20 produces an alert to move system 24. At a fluoroscope moving step 114, the operator of system 10 moves system 24 away from chest position sensors 28a-28c to a larger distance and/or to a different angle, e.g. AP position, until the interference is within allowed magnitude, and subsequently, the method loops back to measured position acquisition step 102.

If processor 20 detects discrepancy in the relative position of the patches and there is no indication of magnetic interference, processor 20 produces an alert to move patient 14. At a patient moving step 116, a clinical operator moves patient 14 so as to correct the map shifting by aligning between respective icons 58 and 60. Subsequently, the method loops back to measured position acquisition step 102.

The configuration of system 10 is depicted by way of example for the sake of conceptual clarity. In alternative embodiments, system 10 may comprise any suitable additional or alternative components and modules configured to enable the embodiments described in FIGS. 1-3 above.

The steps of the method described above may continue iteratively until there are no discrepancies between the predefined and measured values, so that the operator of system 10 may carry out the medical procedure and the method terminates.

Although the embodiments described herein mainly address position tracking in electro-physiological mapping procedures, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for correcting map shifting, comprising:
a processor, which is configured to:
receive electrical signals indicative of measured positions of one or more chest position sensors configured to be attached externally to a chest of a patient, and one or more back position sensors configured to be attached externally to a back of the patient;
compare at least one of (i) the respective measured positions and predefined positions of the one or more chest position sensors, or (ii) the respective measured positions and predefined positions of the one or more back position sensors;
cause an alert to be displayed on an output device in response to detecting a discrepancy between at least one of (i) the respective measured and predefined positions of the one or more chest position sensors, or (ii) the respective measured and predefined positions of the one or more back position sensors;
determine whether magnetic interference from an anatomical imaging system is detected in the electrical signals received by the one or more chest position sensors;
reposition, in response to detecting magnetic interference, the anatomical imaging system away from the one or more chest position sensors until the detected magnetic interference is within an allowable magnitude;
reposition the patient to align at least one of the measured positions and predefined positions of the: i) one or more chest position sensors, or ii) the one or more back position sensors, in response to detecting the discrepancy;
compare, when no magnetic interference is detected or the detected magnetic interference is within an allowable magnitude, received additional electrical signals indicative of measured positions of the one or more chest position sensors and the one or more back position sensors after repositioning the patient until there is no discrepancy.

2. The system according to claim 1, wherein the processor is configured to receive each of the measured positions after receiving the predefined positions.

3. The system according to claim 1, wherein the processor is configured to estimate distances between the measured positions and the respective predefined positions, and to detect the discrepancy based on the estimated distances.

4. The system according to claim 3, wherein the processor is configured to detect the discrepancy by detecting that at least one of the distances between a predefined position and a respective measured position is above a predefined threshold value.

5. The system according to claim 3, wherein the output device is configured to display at least one value of the distances.

6. The system according to claim 1, wherein the processor is configured to indicate on the output device, based on the alert, a responsive action for reducing the discrepancy.

7. The system according to claim 1, wherein the processor is configured to: (i) calculate, based on the predefined positions, a predefined geometrical center-of-gravity (COG), (ii) calculate, based on the measured positions, a measured geometrical COG, (iii) compare the measured geometrical COG with the respective predefined geometrical COG, and (iv) produce the alert in response to detecting a discrepancy between the measured geometrical COG and the predefined geometrical COG.

8. A method for correcting map shifting, comprising:
receiving electrical signals indicative of measured positions of one or more chest position sensors configured to be attached externally to a chest of a patient, and one or more back position sensors configured to be attached externally to a back of the patient;
comparing at least one of (i) the respective measured positions and predefined positions of the one or more chest position sensors, or (ii) the respective measured positions and predefined positions of the one or more back position sensors;
cause an alert to be displayed on an output device in response to detecting a discrepancy between at least one of (i) the respective measured and predefined positions of the one or more chest position sensors, or (ii) the respective measured and predefined positions of the one or more back position sensors;
determining whether magnetic interference from an anatomical imaging system is detected in the electrical signals received by the one or more chest position sensors;
repositioning, in response to detecting magnetic interference, the anatomical imaging system away from the one or more chest position sensors until the detected magnetic interference is within an allowable magnitude;
repositioning the patient to align at least one of the measured positions and predefined positions of the: i) one or more chest position sensors, or ii) the one or more back position sensors, in response to detecting the discrepancy;
comparing, when no magnetic interference is detected or the detected magnetic interference is within an allowable magnitude, received receiving additional electrical signals indicative of measured positions of the one or more chest position sensors and the one or more back position sensors after repositioning the patient until there is no discrepancy.

9. The method according to claim 8, wherein receiving the electrical signals comprises receiving each of the measured positions after receiving the predefined positions.

10. The method according to claim 8, wherein comparing between the measured positions and respective predefined positions comprises estimating distances between the measured positions and the respective predefined positions, and wherein producing the alert comprises detecting the discrepancy based on the estimated distances.

11. The method according to claim 10, wherein detecting the discrepancy comprises detecting that at least one of the distances between a predefined position and a respective measured position is above a predefined threshold value.

12. The method according to claim 10, wherein outputting the alert comprises displaying at least one value of the distances.

13. The method according to claim 8, further comprising indicating on the output device, based on the alert, a responsive action for reducing the discrepancy.

14. The method according to claim 8, wherein comparing between the measured positions and the respective predefined positions comprises: (i) calculating, based on the predefined positions, a predefined geometrical center-of-gravity (COG), (ii) calculating, based on the measured positions, a measured geometrical COG, and (iii) comparing the measured geometrical COG with the respective predefined geometrical COG; and wherein producing the alert comprises producing the alert in response to detecting a discrepancy between the measured geometrical COG and the predefined geometrical COG.

15. A non-transitory computer-readable medium having computer-readable instructions embodied therein to be executed by one or more processors, the instructions causing the one or more processors to:
  receive electrical signals indicative of measured positions of one or more chest position sensors configured to be attached externally to a chest of a patient, and one or more back position sensors configured to be attached externally to a back of the patient;
  compare at least one of (i) the respective measured positions and predefined positions of the one or more chest position sensors, or (ii) the respective measured positions and predefined positions of the one or more back position sensors;
  cause an alert to be displayed on an output device in response to detecting a discrepancy between at least one of (i) the respective measured and predefined positions of the one or more chest position sensors, or (ii) the respective measured and predefined positions of the one or more back position sensors;
  determine whether magnetic interference from an anatomical imaging system is detected in the electrical signals received by the one or more chest position sensors;
  reposition, in response to detecting magnetic interference, the anatomical imaging system away from the one or more chest position sensors until the detected magnetic interference is within an allowable magnitude;
  reposition the patient to align at least one of the measured positions and predefined positions of the: i) one or more chest position sensors, or ii) the one or more back position sensors, in response to detecting the discrepancy;
  compare, when no magnetic interference is detected or the detected magnetic interference is within an allowable magnitude, received additional electrical signals indicative of measured positions of the one or more chest position sensors and the one or more back position sensors after repositioning the patient until there is no discrepancy.

16. The non-transitory computer-readable medium according to claim 15, wherein the computer-readable instructions include further instructions to receive each of the measured positions after receiving the predefined positions.

17. The non-transitory computer-readable medium according to claim 15, wherein the computer-readable instructions include further instructions to estimate distances between the measured positions and the respective predefined positions, and to detect the discrepancy based on the estimated distances.

18. The non-transitory computer-readable medium according to claim 17, wherein the computer-readable instructions include further instructions to further instructions to detect the discrepancy by detecting that at least one of the distances between a predefined position and a respective measured position is above a predefined threshold value.

19. The non-transitory computer-readable medium according to claim 17, wherein the output device is configured to display at least one value of the distances.

20. The non-transitory computer-readable medium according to claim 15, wherein the computer-readable instructions include further instructions to: (i) calculate, based on the predefined positions, a predefined geometrical center-of-gravity (COG), (ii) calculate, based on the measured positions, a measured geometrical COG, (iii) compare the measured geometrical COG with the respective predefined geometrical COG, and (iv) produce the alert in response to detecting a discrepancy between the measured geometrical COG and the predefined geometrical COG.

* * * * *